United States Patent [19]

Shoesmith

[11] Plant 4,289

[45] Aug. 8, 1978

[54] CHRYSANTHEMUM PLANT NAMED LOYALTY

[75] Inventor: Leonard H. Shoesmith, Westfield-Woking, England

[73] Assignee: Pan-American Plant Company, West Chicago, Ill.

[21] Appl. No.: 783,013

[22] Filed: Mar. 30, 1977

[51] Int. Cl.[2] ..... A01H 5/00

[52] U.S. Cl. ..... Plt./76

[58] Field of Search ..... Plt./76, 81

*Primary Examiner*—Robert E. Bagwill

*Assistant Examiner*—James R. Feyrer

*Attorney, Agent, or Firm*—Chas. W. Rummler

[57] ABSTRACT

A new and distinct variety of chrysanthemum plant for greenhouse culture, characterized by the decorative form of its medium to large flowers with ray florets of deep pink which surround a central mass of closely grouped purple florets; by its year around 9-week response as a pot plant, its good breaking ability, its very dense, dark green foliage, and its tolerance to high soluble salt conditions.

2 Drawing Figures

BACKGROUND OF THE NEW PLANT

This new chrysanthemum plant variety originated as a seedling of unidentified parentage which was discovered by me in 1972 among a group of plants grown by me at Westfield-Woking, Surrey, England, for breeding purposes. The unusual and lovely coloration of the blossoms of this plant and the dense growth of its foliage caused me to propagate the plant by cuttings for observation and test. Propagation of this new plant through successive generations, in my greenhouses at Westfield-Woking, Surrey, England, by vegetative cuttings has shown this plant to not only have considerable merit for commercial exploitation but also that its distinctive characteristics hold true from generation to generation and appear to be firmly fixed. This plant is now being asexually propagated and grown at West Chicago, Ill., and at Cortez, Fla., with full retention of all of its original distinctive characteristics.

DESCRIPTION OF THE DRAWING

My new chrysanthemum plant is illustrated by the accompanying full color photographic drawing, which shows the form and color characteristics of the flowers, and by a machine copied drawing showing photoprints of typical leaves of the new plant taken from representative positions along the plant stems. The photographic drawing shows the flower colors of the new plant as faithfully as it is reasonably possible to obtain by conventional professional photographic procedures.

DESCRIPTION OF THE NEW PLANT

The following is a detailed description of my new variety of chrysanthemum based upon observations at West Chicago, Ill., and with color designations according to the R.H.S. Colour Chart published by The Royal Horticultural Society of London, England, with collaboration of The British Colour Council.

THE PLANT

Origin: Seedling.

Parentage: Both seed parent and pollen parent are unidentified plants.

Classification:

*Botanic.*—*Chrysanthemum morifolium.*

*Commercial.*—Greenhouse pot plant.

Form: Perennial herbaceous bush.

Height: 11 to 16 inches.

Growth: Terminal, upright and vigorous; sturdy and with very good strength, the photograph having been taken in September 1976.

Branching: Normal.

Foliage: Quantity — abundant with 9 to 12 leaves on 4 inches of stem.

*Leaf size.*—$2\frac{1}{4}$ to $3\frac{3}{4}$ inches long and $1\frac{5}{8}$ to $2\frac{3}{8}$ inches wide.

*Leaf shape.*—Lobed — lanceolate with deeply serrated margins.

*Surface aspect.*—Canescent.

*Venation.*—Pinnately veined.

*Color.*—Upper side — RHS 147A. Under side — RHS 147B.

*Petioles.*—$\frac{1}{8}$ to $\frac{1}{2}$ inch long.

THE BUD

Form: Globular.

Size:

*Diameter.*—$\frac{1}{2}$ to $\frac{3}{4}$ inch.

*Depth.*—$\frac{3}{8}$ to $\frac{5}{8}$ inch.

Opening rate: Slow.

Color:

*When phyllaries first divide.*—RHS 144B on outside.

*When florets begin to unfurl.*—RHS 59B to 64A to 71A depending upon season of flowering.

Phyllaries: The outside of the receptacle bears many involucral bracts which are spear-shaped and upstanding.

*Color.*—Inside — RHS 137B. Outside — RHS 137B.

*Surface aspect.*—Pubescent.

Peduncle: Upright and $\frac{3}{4}$ to $1\frac{5}{8}$ inches long.

*Surface aspect.*—Pubescent.

THE FLOWER

Recommended flowering: The year around with photoperiod control.

Response: 9-week.

Natural flowering season: October 25 to November 2.

Blooms: Flower type — composite and decorative.

*Borne.*—A head of many florets carried on a receptacle.

*Size.*—Medium-large. Diameter — $2\frac{3}{4}$ to $3\frac{3}{4}$ inches. Depth — $1\frac{1}{8}$ to $1\frac{3}{8}$ inches.

*Shape.*—Flat when bloom first opens, becoming high centered with outer petals reflexing downward as bloom matures.

*Florets.*—Number — numerous. Form: Linear with obtuse apex. Color: Outer florets: Upper side — RHS 60D, 64B, 71C. Reverse side — RHS 70C, 74C, 74D. Inside florets: Upper side — RHS 64B, 71B. Reverse side — RHS 70B, 70C, 74D. Firmness: Medium. Appearance: Slightly shiny. Discoloration: A moderate fade after full bloom.

*Peduncle.*—Sturdy and upright, $\frac{3}{4}$ to $1\frac{5}{8}$ inches long. Color: RHS 147B.

Persistence: Florets hang on and dry.

Fragrance: Typical chrysanthemum.

Lasting quality:

*On plant.*—3 weeks.

*As a cut flower.*—Not recommended.

REPRODUCTIVE ORGANS

Stamens:

*Arrangement.*—5 syngenesious stamens.

*Filaments.*—Length — 1/16 to $\frac{1}{8}$ inch. Color: Light yellow.

*Pollen.*—Yellow.

Pistils:

*Number.*—One for each ray and disc floret.

*Styles.*—Length — $\frac{1}{8}$ to 3/16 inch.

*Stigmas.*—Color — Yellow.

Ovaries: Inferior bicarpellate.

This new variety of chrysanthemum plant is not recommended for cut flowers or other than greenhouse culture. As a pot plant, however, it grows with strong, erect stems, good breaking ability, with 4 to 5 lateral breaks when manually pinched, and with a very dependable year around 9-week response. The blooms have excellent decorative flower form, medium to large flower size, and a lovely deep pink coloration with only a moderate fade under high light conditions. The foliage of this plant is very dense with a dark green color and the plant has good tolerance to high soluble salt conditions.

I claim:

1. A new and distinct variety of chrysanthemum plant, substantially as herein shown and described, characterized by its profuse production of deep pink flowers of medium to large size and composite and decorative form, its year around flowering ability and very dependable 9-week response to photoperiod control, and by its growth habit of producing strong and erect stems with good breaking ability and very dense foliage.

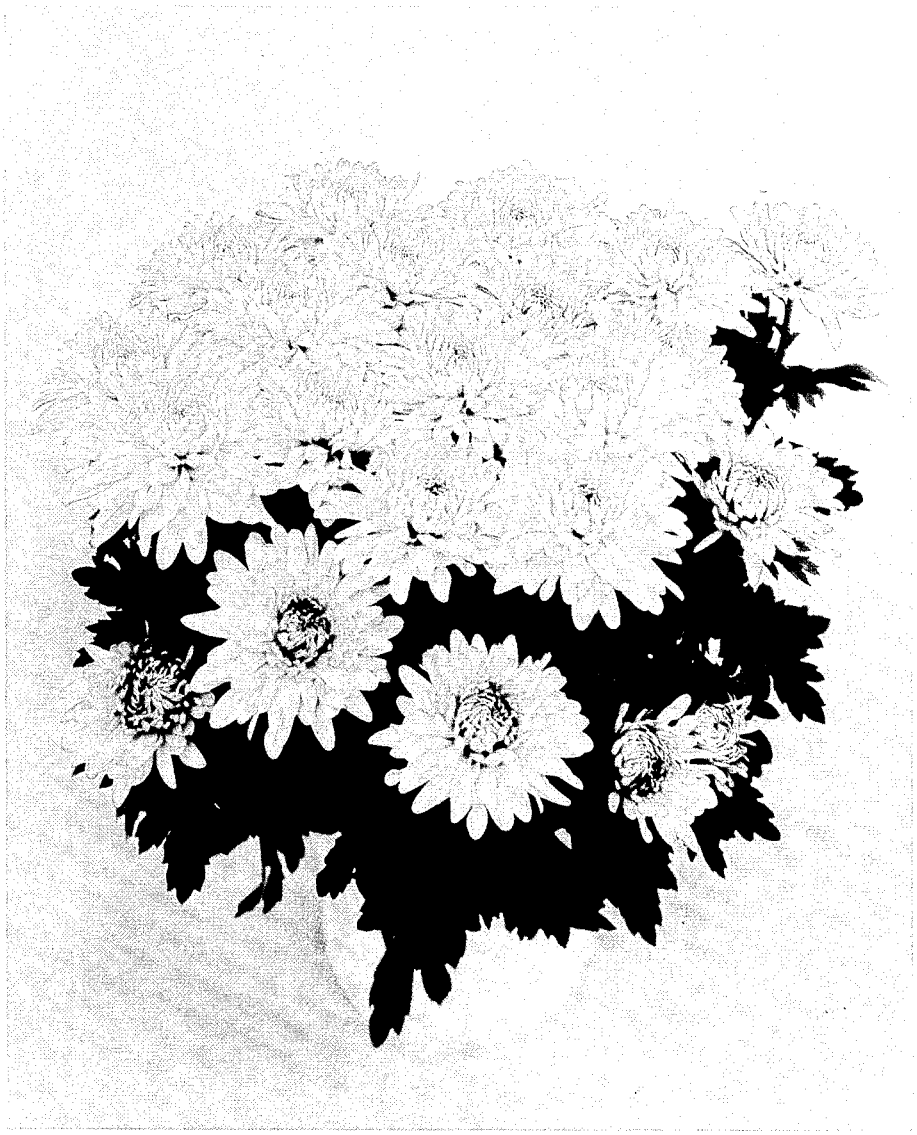

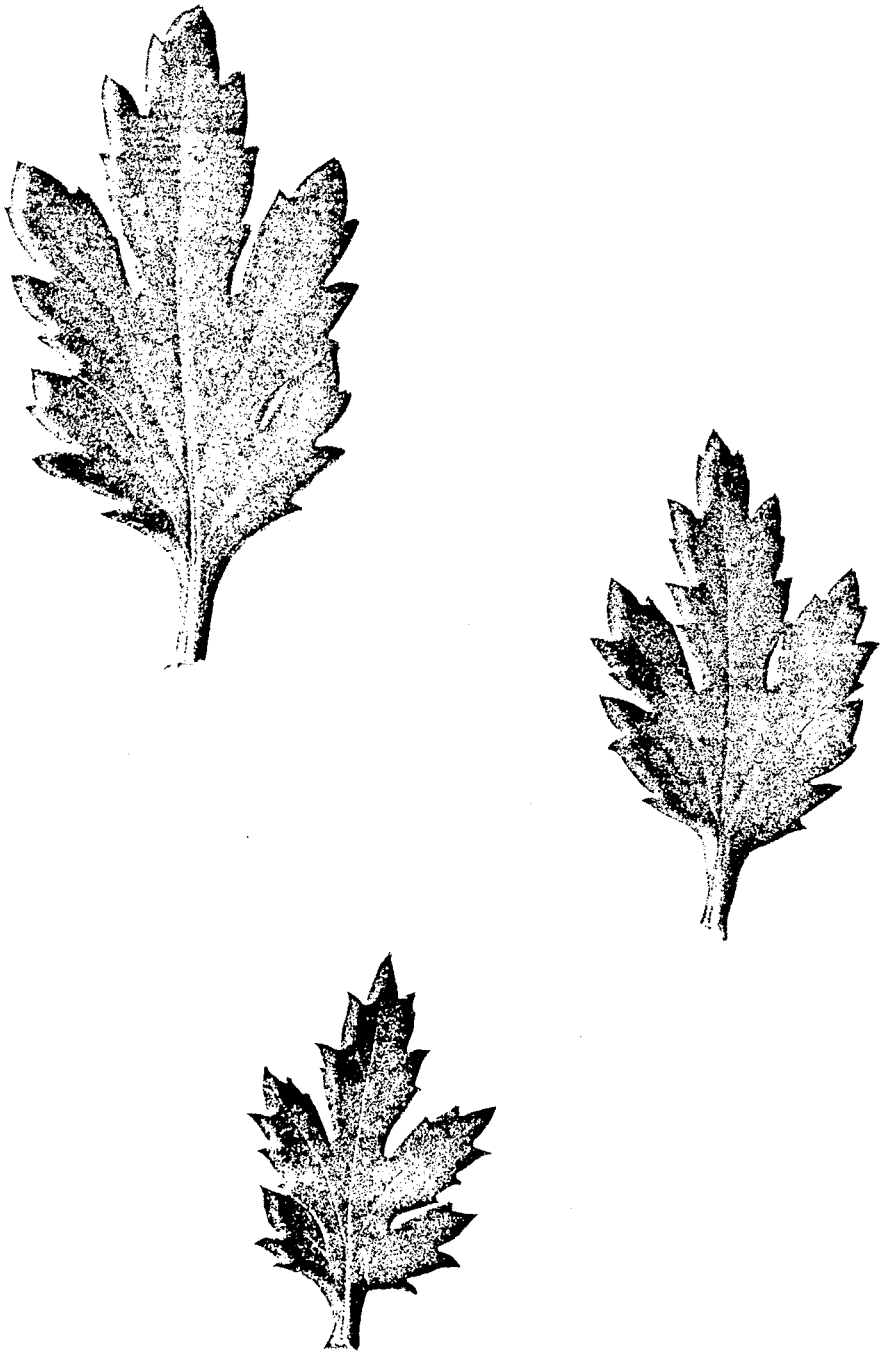

* * * * *